United States Patent [19]

Albonetti et al.

[11] Patent Number: 5,663,392
[45] Date of Patent: Sep. 2, 1997

[54] PREPARATION OF $VSB_ATI_BO_x$ AMMOXIDATION CATALYSTS

[75] Inventors: Stéfania Albonetti, Imola, Italy; Gilbert Blanchard, Le Plessis Belleville; Paolo Burattin, Paris, both of France; Fabrizio Cavani, Modena; Ferruccio Trifiro, Bologna, both of Italy

[73] Assignee: R.P. Fiber & Resin Intermediates, Courbevoie Cedex, France

[21] Appl. No.: 590,577

[22] Filed: Jan. 24, 1996

[30] Foreign Application Priority Data

Jan. 24, 1995 [FR] France ........................ 95 00999

[51] Int. Cl.⁶ ........................................ C07F 9/90
[52] U.S. Cl. ........................ 556/28; 556/29; 558/319
[58] Field of Search ................ 556/28, 29; 558/319

[56] References Cited

U.S. PATENT DOCUMENTS 4,162,992  7/1979  Wise .
5,258,543  11/1993  Suresh et al. .

FOREIGN PATENT DOCUMENTS 0003158   7/1979  European Pat. Off. .
0492805   7/1992  European Pat. Off. .
92 01631  2/1992  WIPO .

*Primary Examiner*—Johann Richter
*Assistant Examiner*—John Peabody
*Attorney, Agent, or Firm*—Burns, Doane, Swecker & Mathis, L.L.P.

[57] ABSTRACT

Mixed oxide vanadium/antimony/titanium ammoxidation catalysts, particularly suited for the ammoxidation of alkanes and exhibiting X-ray diffraction spectra which are characteristic of a crystallographic phase of rutile $TiO_2$, are prepared by (a) dissolving respective soluble compounds of vanadium, of antimony and of titanium in at least one saturated alcohol, (b) contacting the alcoholic solution thus obtained with water and precipitating the mixed oxide therefrom, and (c) separating and calcining the mixed oxide thus precipitated.

14 Claims, No Drawings

PREPARATION OF VSB$_A$ATI$_B$O$_X$ AMMOXIDATION CATALYSTS

BACKGROUND OF THE INVENTION

1. Technical Field of the Invention

The present invention relates to the synthesis of mixed vanadium, antimony and titanium oxides comprising a crystalline phase of rutile TiO$_2$ type, and to catalysts comprised thereof, for the ammoxidation of alkanes.

2. Description of the Prior Art

Certain mixed vanadium and antimony oxides or mixed oxides of vanadium, antimony and other metals are known compositions which are described, among numerous other mixed oxides, in FR-A-2,072,334.

Similarly, EP-A-0,492,805 describes the preparation of a wide variety of compounds, including mixed oxides of vanadium, antimony, tin and titanium, by mixing compounds of the several metals in an aqueous solution of hydrogen peroxide, subsequently calcining said mixture at a temperature greater than 750° C., preferably greater than 780° C., then treating the calcined mixture with a monohydroxy or dihydroxy compound. All of these compounds have a Ti/V molar ratio of 0.1 or 0.2.

SUMMARY OF THE INVENTION

A major object of the present invention is the provision of an improved process for the preparation of a mixed oxide containing vanadium, antimony and titanium values, corresponding to the general empirical formula (I):

$$VSb_aTi_bO_x \qquad (I)$$

in which a is an integer or fractional number equal to or greater than 0.1, b is an integer or fractional number equal to or greater than 0.1, and x is an integer or fractional number determined by the oxidation states of the other elements, comprising (a) dissolving the respective soluble compounds of vanadium, of antimony and of titanium in at least one saturated alcohol, (b) contacting the alcoholic solution thus obtained with water, whereby precipitating the mixed oxide, and (c) separating the mixed oxide thus precipitated and calcining same.

DETAILED DESCRIPTION OF BEST MODE AND SPECIFIC/PREFERRED EMBODIMENTS OF THE INVENTION

More particularly according to the present invention, the subject mixed oxides exhibit X-ray diffraction lines which are characteristic of a crystallographic phase of rutile TiO$_2$ type and do not exhibit X-ray diffraction lines which are characteristic of the crystallographic phases of α-Sb$_2$O$_4$, cervantite, and/or of Sb$_6$O$_{13}$.

The characteristic lines of the phase of rutile TiO$_2$ type correspond to the following lattice spacings or parameters d (in Å):

3.24–3.27
2.48–2.52
2.29–2.31
2.18–2.21
2.05–2.07
1.68–1.70
1.62–1.64
1.48–1.51
1.45–1.50
1.42–1.46
1.36–1.37
1.30–1.31
1.24–1.26

The characteristic lines of the α-Sb$_2$O$_4$ (cervantite) phase correspond to the following lattice spacings d (in Å):

4.45
3.45
3.07
2.93
2.73
2.65
2.47
2.40
2.24
2.16
2.00
1.91
1.86
1.78
1.72
1.63
1.59
1.56
1.52
1.47
1.42
1.37

The characteristic lines of the Sb$_6$O$_{13}$ phase correspond to the following lattice spacings d (in Å):

5.95
3.11
2.97
2.58
2.36
2.10
1.98
1.82
1.74
1.57
1.55
1.48
1.44

Among the mixed oxides of formula (I) described above, which are prepared by the process of the invention, preferred are those in which:

(i) a represents an integer or fractional number equal to or less than 100;

(ii) b represents an integer or fractional number equal to or less than 100; and (iii) x represents an integer or fractional number determined by the oxidation state of the other elements.

Lastly, more particularly preferred are the mixed oxides of formula (I), in which:

(i') a is an integer or fractional number ranging from 0.5 to 50; (ii') b is an integer or fractional number ranging from 1 to 40; and (iii') x is an integer or fractional number determined by the oxidation state of the other elements.

The vanadium, antimony and titanium compounds employed in the process must be soluble in a saturated alcohol or a mixture of saturated alcohols. As utilized herein, a compound is regarded as "soluble" when its solubility, measured at 25° C., is at least 5 grams per liter of saturated alcohol. These compounds can be introduced together; they can also first be dissolved separately in an alcohol, the separate alcoholic solutions thus obtained being subsequently mixed with one another. Generally, but without limitation, an alcoholic solution is prepared by dissolving the various compounds, without intermediate preparation of solutions of each of the vanadium, antimony and titanium compounds.

Exemplary soluble vanadium compounds which are representative include vanadyl acetylacetonate, vanadyl trichloride, vanadium trifluoride, vanadium tetrafluoride, vanadium pentafluoride, vanadium tribromide, vanadium dichloride, vanadium trichloride, vanadium tetrachloride and vanadium triiodide.

Exemplary soluble antimony compounds which are representative include antimony pentachloride, antimony trichloride, antimony tribromide, antimony trifluoride, antimony triiodide, antimony trioxide and antimony hydride.

And exemplary soluble titanium compounds which are representative include titanium dichloride, titanium tetrachloride, titanium trichloride, titanium tribromide, titanium tetrabromide, titanium tetrafluoride and titanium diiodide.

The saturated alcohols employed in the process of the invention are, more particularly, alkanols and cycloalkanols. It is preferred to use alkanols and cycloalkanols whose boiling point is not excessively high, in order to facilitate the operations of separation or of recycling by distillation or evaporation. Consequently, alkanols having from 1 to 6 carbon atoms, such as methanol, ethanol, n-propanol, 2-propanol, n-butanol, 2-butanol, tert-butanol, pentanols and hexanols, and cyclohexanol, are preferred.

The alcoholic solution thus obtained is then mixed with water, to precipitate the mixed oxides. The operation is preferably carried out in an aqueous solution of an ammonium salt, in particular an ammonium carboxylate (for example the acetate, citrate or tartrate), ammonium oxalate, ammonium carbonate or ammonium hydrogen phosphate, which provides a pH of from 5 to 9 and preferably of about 7. Thus ammonium acetate at a concentration of two mol per liter in water has a pH of approximately 7.

To maintain the pH of this solution preferably at a value of close to 7, it may be necessary to progressively neutralize the acidity which is possibly formed during the precipitation of the mixed oxides (for example, hydrohalic acid formed when an antimony halide and/or a titanium halide and/or a vanadium halide is/are employed) by means of a basic compound. In the process of the invention, it is preferred to carry out this neutralization by the controlled, progressive addition of aqueous ammonia.

After precipitation of the mixed oxides of the invention, they are separated from the saturated alcohol/water liquid medium by any technique which is commonly used for this type of operation, especially by filtration. The isolated mixed oxides are then dried, at atmospheric pressure or under reduced pressure, at a temperature of, for example, from 30° C. to 200° C., these values being of no critical importance.

The mixed oxides of formula (I) are then calcined at a temperature of from 400° C. to 800° C. Calcination is preferably carried out at a temperature of 500° C. to 750° C.

The present invention also features a process for the ammoxidation of alkanes in the vapor phase in the presence of a solid catalyst containing at least one active phase which comprises at least one mixed oxide corresponding to the general empirical formula (I), said at least one mixed oxide being prepared according to the process described above.

In accordance with the present invention, alkanes having from 3 to 12 carbon atoms per molecule are reacted in the vapor phase with ammonia and oxygen, in the presence of a catalyst whose active phase is as described above.

According to the present process, it is of course possible to use diluent gases which are inert under the conditions of reaction, such as helium, nitrogen and argon. Likewise, steam can be added to the gaseous reaction mixture within wide limits. The reactive gas (alkane, ammonia, oxygen) can thus be diluted with an inert diluent and/or with steam. In this respect, the content of steam can vary over wide limits, in particular from 0% to 50% and, preferably, between 3% and 30%. To advantageously carry out the process according to the invention, the content of reactive gas will be at least 3% and preferably at least 20%.

Within the reactive gas, the respective volumetric contents of alkane, ammonia and oxygen can vary over wide limits.

The content of alkane in the reactive gas preferably ranges from 5% to 70%. That of ammonia preferably ranges from 3% to 50%, and that of oxygen preferably ranges from 3% to 45%.

To properly carry out the process according to the invention, the composition of the reactive mixture will preferably be selected such as to be outside the explosive region.

Starting from propane, the mixture obtained will essentially contain propylene and acrylonitrile. Acrylonitrile is an intermediate which is produced industrially on a large scale, while propylene is a raw material which is traditionally used to produce acrylonitrile and various other intermediate compounds which are well known to this art.

Starting from isobutane, the mixture obtained will comprise methacrylonitrile and isobutene or n-butenes.

The process according to the invention is more particularly suited for the ammoxidation of propane.

If the alkane employed can be of technical grade, it will not contain significant amounts of ethylenically unsaturated compounds. Thus, the propane employed will generally contain only minor amounts of propylene, for example less than 10%.

The process according to the invention is carried out as a vapor phase reaction. Consequently, any apparatus suitable for carrying out ammoxidation or oxidation reactions in the vapor phase can be used. The process can be carried out continuously, or batchwise, and it can comprise the use of a fixed bed or of a fluidized bed.

The reaction temperature, in general, ranges from 300° C. to 550° C., and, preferably, from 400° C. to 500° C.

The total pressure of the reaction mixture may be greater than or equal to atmospheric pressure. It generally ranges from 1 to 6 bar, and, preferably, from 1 to 4 bar.

The gas flow rate is established such that the hourly volume rate advantageously ranges from 100 to 36,000 $h^{-1}$, and, preferably, from 200 to 20,000 $h^{-1}$.

The hourly volume rate is defined as the ratio total gas volume/volume of catalyst/hour.

One skilled in this art will of course establish a compromise between the temperature, the gas flow rate, the precise nature of the catalyst employed and the various other parameters of the reaction, taking account of the various production objectives.

The catalyst which is used in the process for the ammoxidation of alkanes can comprise only one or a number of the mixed vanadium, antimony and titanium oxides described above, as the active phase of the catalyst, or can additionally comprise an inorganic oxide such as, for example, alumina, silica, silica/alumina, zirconia, cerite, magnesia, titanium dioxide or niobium oxide, on which said active phase is deposited or with which the active phase is mixed, utilizing various techniques which are known to this art, such as impregnation or slurry deposition.

The catalytic phase, comprising the active phase alone or the active phase deposited onto an inorganic oxide, or mixed with said inorganic oxide, can then be employed in bulk form or in the particulate state; it can therefore be used in powder form or can be shaped, for example as beads or spheres, pellets, extrudates or crushed particles, according to various known techniques.

To carry out the process in a fixed bed, examples of possible such techniques are pelletizing or coating onto an inert substrate or onto a ceramic or metal substrate of monolithic type.

To carry out the process in a moving bed or in a fluidized bed, the catalytic phase is generally shaped by atomizing, drying and calcining.

The catalytic phases can, for example, be shaped by compression to provide pellets. These pellets can then optionally be crushed to convert same into fragments. The precise values for the pressure, the diameter and thickness of the pellets and the particle size of the fragments can be selected by one skilled in this art according to the pressure drop which is acceptable in the reactor.

One embodiment for the preparation of the catalytic phase can entail, in a single stage, the synthesis of the active phase and the deposition thereof onto an inorganic oxide or the mixing thereof with said inorganic oxide.

The catalytic phases can also be deposited onto an inert substrate or can be coated. The nature of this substrate is not critical, provided that it is chemically inert with regard to the reactants under the selected reaction conditions. Exemplary substrates suitable for the preparation of catalysts which can be used in the context of the process according to the invention are silica, alumina, silica/alumina, sintered clay, carborundum, magnesia, magnesium silicate and diatomaceous earth. This substrate is preferably nonporous and can in particular be based on refractory oxide in the particulate form, the most typically employed substrate being clay-based. This substrate can, for example, comprise inert, complete, solid and rough clay beads having a diameter ranging from 0.5 to 6 mm.

The precise diameter of the beads will be selected according to the pressure drop which is acceptable in the reactor. This substrate can also be rendered nonporous by enamelling.

This substrate can also be a ceramic substrate and, in which event, is preferably in the form of an inert and rigid structure of monolithic type comprising channels or ducts. Supports of this nature are well known to this art and are widely described in the literature. The substrates fabricated from ceramic materials are, in particular, those comprising cordierite, alumina, mullite, porcelain or the carbides of boron or of silicon as the principal constituent.

This substrate may also be a metal substrate. Such substrates too are well known to this art. Suitable metal substrates are, in particular, those fabricated from alloys of iron, nickel and chromium, or those fabricated from alloys of iron, chromium, aluminum and cobalt, such as those marketed under the trademark KANTHAL, or those fabricated from alloys of iron, chromium, aluminum and yttrium, which are marketed under the trademark FECRALLOY. The metal may also be carbon steel, or simple cast iron.

When a coated catalyst is employed, the amount of catalytic phase can vary over wide limits and advantageously ranges from 1% to 50%, and preferably from 5% to 35%, by weight relative to the overall combination of substrate+catalytic phase.

Thus, certain catalysts which are useful for carrying out the subject process in the fixed bed can be obtained by coating the crushed, intermediate or finished, catalytic phases in a manner per se known to this art. This conventional technique entails depositing a layer of intermediate or finished catalytic phase around inert but rough beads. Once the beads have been coated with the desired amount of catalytic phase, they are dried in hot air at a temperature ranging from 70° to 150° C. for at least 30 minutes, then introduced into an oven to be calcined at a temperature of from 300° to 600° C., preferably from 450° to 500° C., for at least 3 hours.

Certain catalysts which are useful for carrying out the process according to the invention in a moving bed or in a fluidized bed can be obtained by the technique, also per se known to this art, of spray-drying in a preferably nonreducing atmosphere. By means of such an operation, followed if appropriate by calcining at a temperature on the order of from 400° to 800° C., powders are obtained which are spherical in shape and have a diameter ranging from 5 to 700 µm. Powders comprising at least 80% by weight of particles having a size of from 5 to 200 µm are preferred in the context of use in a fluidized bed.

The catalytic phase, whether alone or thus employed in bulk state, or in the particulate state, constitutes the catalyst.

The products of the reaction can be recovered from the effluent gases by any appropriate means. For example, the effluent gases can be transferred into a condenser containing dilute sulfuric acid in order to neutralize the unreacted ammonia. The gases can then be charged through a refrigerated absorbing column in order to condense the acrylonitrile, acetonitrile and hydrocyanic acid, the uncondensed vapors principally containing unreacted propane, propylene, light hydrocarbons and, if appropriate, $CO_2$. The acrylonitrile and hydrocyanic acid can then be separated from the acetonitrile by distillation, and the acrylonitrile/ hydrocyanic acid mixture recovered can in turn be distilled to separate the acrylonitrile from the hydrocyanic aid.

In order to further illustrate the present invention and the advantages thereof, the following specific examples are given, it being understood that same are intended only as illustrative and in nowise limitative.

EXAMPLE 1

Preparation of the mixed oxide (A) according to the invention, having the empirical formula $VSb_5Ti_5O_x$:

A solution of 10.92 g of anhydrous $TiCl_4$, 3.05 g of vanadyl acetylacetonate and 17.22 g of $SbCl_5$ in 100 ml of absolute ethanol was prepared.

The ethanolic solution was poured dropwise into 500 ml of an aqueous solution containing ammonium acetate (2 mol/liter) to provide an initial pH on the order of 7.0. During precipitation of the mixed V, Sb and Ti oxides, the pH, which tended to decrease by reason of the liberation of hydrochloric acid, was maintained constant by adding concentrated aqueous ammonia solution (30% strength by weight).

The precipitate thus formed was isolated by filtration, washed with water, dried for 12 h at 140° C. and then calcined for 3 h at 700° C.

The compound of formula $VSb_5Ti_5O_x$ thus obtained was subsequently compressed under a pressure of 4,300 bars.

Pellets having a diameter of 3 cm and a thickness of approximately 0.5 cm were then obtained. These pellets were crushed into fragments having a particle size of from 0.3 to 0.8 cm, constituting the catalyst (A) according to the invention.

EXAMPLES 2 AND 3

Preparation of various mixed oxides according to the invention:

Various mixed oxides were prepared by the procedure described in Example 1, but using different amounts of vanadyl acetylacetonate (Example 3) or antimony pentachloride (Example 2).

Mixed oxides according to the invention were thus obtained, having the following formulae:

Example 2: $VSb_{10}Ti_5O_x$ (reference D)

Example 3: $VSb_{10}Ti_{10}O_x$ (reference E)

COMPARATIVE TEST 1

Preparation of the mixed oxide (B) via a prior art process, having the empirical formula $VSb_5Ti_5O_x$:

The mixed oxide of composition $VSb_5Ti_5O_x$ was prepared in three stages by coprecipitation in an aqueous medium.

9.52 g of titanium tetrachloride were dissolved in 100 ml of an $HCl/H_2O$ solution having a pH of 0.5–1.0. The solution was maintained at a low temperature by means of an ice/water bath. It was then heated to 90° C., and this temperature was maintained for 1 hour.

In a second solution similar to that above, 2.65 g of vanadyl acetylacetonate and 15.0 g of antimony pentachloride were dissolved. This solution was then poured into a buffer solution of ammonium acetate whose pH was maintained constant at approximately 7 by addition of aqueous ammonia.

The two solutions thus prepared were mixed and were maintained under stirring for 30 minutes. The mixed oxide which precipitated was separated off by centrifugation, washed, dried at 140° C. for 12 hours and then calcined for 3 hours at 700° C.

The compound of formula $VSb_5Ti_5O_x$ thus obtained was then compressed under a pressure of 4,300 bars. Pellets having a diameter of 3 cm and a thickness of approximately 0.5 cm were then obtained. These pellets were crushed into fragments having a particle size of from 0.3 to 0.8 cm, constituting the catalyst (B) not according to the invention.

COMPARATIVE TEST 2

Preparation of the mixed oxide (J) via a prior art process, having the empirical formula $VSb_5Ti_5O_x$:

The mixed oxide of composition $VSb_5Ti_5O_x$ was prepared by the procedure described in Example M of U.S. Pat. No. 5,008,427.

The compound of formula $VSb_5Ti_5O_x$ thus obtained was then compressed under a pressure of 4,300 bars. Pellets having a diameter of 3 cm and a thickness of approximately 0.5 cm were then obtained. These pellets were crushed into fragments having a particle size of from 0.3 to 0.8 cm, constituting the catalyst (J) not according to the invention.

EXAMPLES 4 TO 6

Preparation of various mixed oxides according to the invention:

Various mixed oxides were prepared by the procedure described in Example 1, but using different amounts of vanadyl acetylacetonate, titanium tetrachloride or antimony pentachloride.

Mixed oxides according to the invention were thus obtained, having the following formulae:

Example 4: $VSbTi_{6.7}O_x$ (reference F)

Example 5: $VSb_{1.5}Ti_{0.2}O_x$ (reference H)

Example 6: $VSb_{1.5}Ti_1O_x$ (reference I)

Characterization Of The Mixed Oxides Prepared:

The various mixed oxides A, D, E, F, H and I according to the invention and B not according to the invention were characterized by X-ray diffraction using a PHILIPS P1800 diffractometer in the measurement range 10° to 70° in 2θ. The characteristic lines of the various oxides were then compared with the characteristic lines of the pure products, reported in International Tables of X-Ray crystallography.

The diffraction patterns obtained demonstrated clearly that the catalysts (A), (D) and (E) were composed of a rutile phase whose unit cell parameters were very similar to those of rutile $TiO_2$. The diffraction pattern for the oxide (B) of the prior art showed that the oxide (B) was composed of a rutile $TiO_2$ phase and of the oxide $Sb_6O_{13}$.

General Procedure For The Ammoxidation Tests:

The catalyst sample was heated beforehand on a measuring bench to a temperature of 150° C. while being purged with helium for 10 min, and was then subjected to a gas flow whose composition will be specified for each example and which comprised propane, ammonia, oxygen, helium and, if appropriate, steam.

The total pressure of the reaction mixture was between 1 and 6 bars and will likewise be specified for each example.

The total gas flow rate is defined such that the hourly volume rate (HBR) ranged from 100 to 36,000 $h^{-1}$, the precise value of which will be indicated below for each example.

Volume of active phase: 25 $cm^3$.

The principle of the ammoxidation test for propane was as follows:

(a) The catalyst was heated to a temperature $T_1$, for example 310° C., and, after stabilization for 30 min at the temperature $T_1$, the composition of the mixture at the reactor outlet was determined by gas chromatography.

(b) The percentage conversions and the selectivities obtained with the catalyst examined at the inlet temperature $T_1$ were calculated by relationships of the type:

conversion of propane (mol %)=propane converted/propane introduced selectivity for acrylonitrile (mol %)=propane converted to acrylonitrile/propane converted.

(c) The catalyst was then heated from 310° to 550° C. in 20° C. steps, and the percentage conversions and selectivities were determined every 40 min.

In the ammoxidation examples below, the following conventions are utilized:

$DC(C_3H_8)$=conversion of propane $S(ACN)$=selectivity for acrylonitrile $S(ACN+C_3H_6)$=selectivity for acrylonitrile and propylene $S(ammox)$=selectivity for acetonitrile, hydrocyanic acid and other ammoxidation byproducts prod. ACN=productivity in terms of acrylonitrile, expressed in g of acrylonitrile formed/liter of catalyst x hour.

The balance to 100% of the selectivities corresponds to the formation of CO and $CO_2$ and, where appropriate, of methane, ethane and ethylene.

Ammoxidation of Propane:

EXAMPLES 7 TO 12 AND COMPARATIVE TESTS 3 AND 4

Ammoxidation of propane was carried out as described above using, as catalysts, the active phases of which being the mixed oxides A, D, E, F, H and I of the invention, and the mixed oxides B and J not according to the invention.

The specific conditions employed were as follows:

(i) Hourly volume rate=1,700 $h^{-1}$ (ii) Total pressure=1.3 bars (iii) Composition by volume of the reaction mixture:
$C_3H_8$=25%
$NH_3$=10%
$O_2$=20%
He=45%

The temperature conditions and the results obtained are reported in the Table below:

TABLE

| Examples | Catalyst used | Temp (°C.) | DC ($C_3H_8$) (in %-) | S(ACN) (in %) | S(ACN + $C_3H_6$) (in %) | S (ammox) (in %) | prod. ACN (g/l × h) |
|---|---|---|---|---|---|---|---|
| Example 7 | A | 388 | 6 | 25 | 31 | 42 | 15 |
| | | 408 | 11 | 34 | 39 | 28 | 37 |
| | | 428 | 22 | 36 | 39 | 14 | 79 |
| | | 447 | 24 | 43 | 46 | 15 | 102 |
| Example 8 | D | 404 | 12 | 40 | 48 | 23 | 48 |
| | | 422 | 14 | 46 | 51 | 21 | 71 |
| | | 442 | 16 | 53 | 56 | 16 | 83 |
| | | 461 | 18 | 53 | 57 | 15 | 95 |
| Example 9 | E | 407 | 13 | 32 | 38 | 25 | 41 |
| | | 426 | 19 | 39 | 43 | 21 | 74 |
| | | 445 | 19 | 49 | 52 | 14 | 92 |
| | | 465 | 19 | 51 | 54 | 14 | 96 |
| Example 10 | F | 407 | 8 | 21 | 48 | 33 | 17 |
| | | 427 | 13 | 25 | 40 | 36 | 32 |
| | | 447 | 17 | 31 | 42 | 23 | 52 |
| | | 468 | 21 | 36 | 43 | 18 | 75 |
| Example 11 | H | 389 | 10 | 29 | 46 | 25 | 29 |
| | | 407 | 14 | 32 | 46 | 23 | 44 |
| | | 428 | 21 | 35 | 47 | 18 | 73 |
| | | 446 | 24 | 37 | 50 | 17 | 88 |
| Example 12 | I | 388 | 15 | 20 | 35 | 30 | 30 |
| | | 408 | 20 | 35 | 45 | 29 | 69 |
| | | 425 | 24 | 37 | 44 | 12 | 88 |
| | | 446 | 25 | 39 | 48 | 7 | 97 |
| Comparative test 3 | B | 424 | 5 | 60 | 83 | 8 | 30 |
| | | 443 | 7 | 58 | 77 | 8 | 40 |
| | | 464 | 9 | 49 | 72 | 6 | 44 |
| | | 485 | 16 | 35 | 57 | 5 | 52 |
| Comparative test 4 | J | 426 | 2 | 22 | 57 | 22 | 4 |
| | | 448 | 3 | 32 | 63 | 21 | 9 |
| | | 468 | 4 | 42 | 67 | 16 | 17 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a mixed oxide containing vanadium, antimony and titanium values and having the empirical formula (I):

$$VSb_aTi_bO_x \qquad (I)$$

in which a is an integer or fractional number equal to or greater than 0.1, b is an integer or fractional number equal to or greater than 0.1, and x is an integer or fractional number determined by the oxidation states of the other elements, comprising (a) dissolving soluble compounds of vanadium, of antimony and of titanium in at least one saturated alcohol, (b) contacting the alcoholic solution thus obtained with water and precipitating the mixed oxide therefrom, and (c) separating the mixed oxide thus precipitated.

2. The process as defined by claim 1, comprising calcining the mixed oxide thus separated.

3. The process as defined by claim 1, wherein formula (I), a is an integer or fractional number equal to or less than 100, b is an integer or fractional number equal to or less than 100, and x is an integer or fractional number determined by the oxidation state of the other elements.

4. The process as defined by claim 1, said soluble vanadium compound comprising vanadyl acetylacetonate, vanadyl trichloride, vanadium trifluoride, vanadium tetrafluoride, vanadium pentafluoride, vanadium tribromide, vanadium dichloride, vanadium trichloride, vanadium tetrachloride or vanadium triiodide.

5. The process as defined by claim 1, said soluble antimony compound comprising antimony pentachloride, antimony trichloride, antimony tribromide, antimony trifluoride, antimony triiodide, antimony trioxide or antimony hydride.

6. The process as defined by claim 1, said soluble titanium compound comprising titanium dichloride, titanium tetrachloride, titanium trichloride, titanium tribromide, titanium tetrabromide, titanium tetrafluoride or titanium diiodide.

7. The process as defined by claim 1, said at least one saturated alcohol comprising an alkanol or cycloalkanol.

8. The process as defined by claim 1, comprising (b) mixing said alcoholic solution with an aqueous solution of an ammonium salt to provide a pH ranging from 5 to 9.

9. The process as defined by claim 8, comprising progressively neutralizing the acidity which is formed during the precipitation of the mixed oxides via addition of a basic compound to the medium of precipitation.

10. The process as defined by claim 2, comprising calcining the mixed oxide at a temperature of from 400° C. to 800° C.

11. The process as defined by claim 1, wherein formula (I), a is an integer or fractional number ranging from 0.5 to 50, b is an integer or fractional number ranging from 1 to 40, and x is an integer or fractional number determined by the oxidation state of the other elements.

12. The process as defined by claim 7, said at least one saturated alcohol comprising an alkanol having from 1 to 6 carbon atoms or cyclohexanol.

13. The process as defined by claim 8, said ammonium salt comprising an ammonium carboxylate, ammonium oxalate, ammonium carbonate or ammonium hydrogen phosphate.

14. The process as defined by claim 8, comprising providing a pH of about 7.

* * * * *